(12) United States Patent
Tekulve et al.

(10) Patent No.: US 8,734,483 B2
(45) Date of Patent: May 27, 2014

(54) SPIDER PFO CLOSURE DEVICE

(75) Inventors: Kurt J. Tekulve, Ellettsville, IN (US); Dusan Pavcnik, Portland, OR (US)

(73) Assignees: Cook Medical Technologies LLC, Bloomington, IN (US); Oregon Health and Science University, Portland, OR (US)

( * ) Notice: Subject to any disclaimer, the term of this patent is extended or adjusted under 35 U.S.C. 154(b) by 1229 days.

(21) Appl. No.: 11/845,423

(22) Filed: Aug. 27, 2007

(65) Prior Publication Data

US 2009/0062844 A1 Mar. 5, 2009

(51) Int. Cl.
*A61B 17/08* (2006.01)

(52) U.S. Cl.
USPC ......... 606/215; 606/213; 606/194; 623/23.72

(58) Field of Classification Search
USPC ........... 623/23.7, 23.72–23.74; 606/213, 215, 606/216, 200, 198; 128/831, 843, 887; 604/104–109
See application file for complete search history.

(56) References Cited

U.S. PATENT DOCUMENTS

| | | | |
|---|---|---|---|
| 3,012,882 | A | 12/1961 | Muldawer et al. |
| 3,174,851 | A | 3/1965 | Buehler et al. |
| 3,772,137 | A | 11/1973 | Tolliver |
| 3,953,566 | A | 4/1976 | Gore |
| 4,662,885 | A | 5/1987 | DiPisa, Jr. |
| 4,665,906 | A | 5/1987 | Jervis |
| 4,675,361 | A | 6/1987 | Ward, Jr. |
| 4,861,830 | A | 8/1989 | Ward, Jr. |
| 4,917,089 | A | 4/1990 | Sideris |
| 5,017,664 | A | 5/1991 | Grasel et al. |
| 5,024,671 | A | 6/1991 | Tu et al. |
| 5,108,420 | A | 4/1992 | Marks |

(Continued)

OTHER PUBLICATIONS

Dušan Pavčnik et al., Monodisk: Device for Percutaneous Transcatheter Closure of Cardiac Septal Defects, CardioVascular and Interventional Radiology, vol. 16, pp. 308-312, 1993.

(Continued)

*Primary Examiner* — David Eastwood
(74) *Attorney, Agent, or Firm* — Brinks Gilson & Lione

(57) ABSTRACT

A device for occluding septal defects or other bodily passageways including PFOs, includes an occluding body formed from a plurality of flexible outwardly radiating occluding wires connected to one or more biocompatible sheet materials. The occluding wires are joined together at proximal wire ends. Linking members connectively link the occluding body to a flexible, substantially linear anchor formed from at least one tube, coil, or bar. The anchor is configured for placement on one side of bodily passageway, whereby the longitudinal axis of at least one anchor extends across a transverse cross-section of the bodily passageway, anchoring the occluding body in place against the other side of a bodily passageway to close, occlude, or fill at least a lumenal portion of a bodily passageway. The anchor may include one or more grasping member(s) integrally formed or connected to the tube, coil, or bar for releasable attachment to an anchor engaging member, such as a biopsy forceps. In a further aspect, a closure device assembly includes a delivery catheter housing a collapsibly disposed closure device linked to a biopsy forceps. The biopsy forceps may be positioned in a locking catheter, which is configured to prevent inadvertent release of the closure device when held in a compressed state inside the delivery catheter. By positioning the catheter near a bodily passageway, such as a PFO, and disengaging the anchor engaging member from the grasping member, the closure device may be released so as to facilitate stable closure of the bodily passageway.

20 Claims, 7 Drawing Sheets

(56) References Cited

U.S. PATENT DOCUMENTS

| | | | |
|---|---|---|---|
| 5,334,217 A | 8/1994 | Das | |
| 5,417,708 A | 5/1995 | Hall et al. | |
| 5,451,235 A | 9/1995 | Lock et al. | |
| 5,589,563 A | 12/1996 | Ward et al. | |
| 5,595,571 A | 1/1997 | Jaffe et al. | |
| 5,643,317 A | 7/1997 | Pavcnik et al. | |
| 5,669,933 A * | 9/1997 | Simon et al. | 600/200 |
| 5,683,411 A | 11/1997 | Kavteladze et al. | |
| 5,690,642 A | 11/1997 | Osborne et al. | |
| 5,720,777 A | 2/1998 | Jaffe et al. | |
| 5,725,534 A | 3/1998 | Rasmussen | |
| 5,733,337 A | 3/1998 | Carr, Jr. et al. | |
| 5,769,796 A | 6/1998 | Palermo et al. | |
| 5,797,953 A | 8/1998 | Tekulve | |
| 5,797,960 A | 8/1998 | Stevens et al. | |
| 5,814,061 A | 9/1998 | Osborne et al. | |
| 5,843,180 A | 12/1998 | Jaffe et al. | |
| 5,843,181 A | 12/1998 | Jaffe et al. | |
| 5,846,247 A | 12/1998 | Unsworth et al. | |
| 5,846,261 A | 12/1998 | Kotula et al. | |
| 5,861,003 A | 1/1999 | Latson et al. | |
| 5,944,738 A | 8/1999 | Amplatz et al. | |
| 5,947,997 A | 9/1999 | Pavcnik et al. | |
| 5,960,642 A | 10/1999 | Kim et al. | |
| 5,980,799 A | 11/1999 | Martakos et al. | |
| 5,993,844 A | 11/1999 | Abraham et al. | |
| 6,063,113 A | 5/2000 | Kavteladze et al. | |
| 6,117,157 A | 9/2000 | Tekulve | |
| 6,206,907 B1 * | 3/2001 | Marino et al. | 606/215 |
| 6,206,931 B1 | 3/2001 | Cook et al. | |
| 6,214,029 B1 * | 4/2001 | Thill et al. | 606/213 |
| 6,251,143 B1 | 6/2001 | Schwartz et al. | |
| 6,346,074 B1 | 2/2002 | Roth | |
| 6,355,052 B1 | 3/2002 | Neuss et al. | |
| 6,358,228 B1 | 3/2002 | Tubman et al. | |
| 6,358,284 B1 | 3/2002 | Fearnot et al. | |
| 6,368,338 B1 | 4/2002 | Konya et al. | |
| 6,371,961 B1 | 4/2002 | Osborne et al. | |
| 6,451,052 B1 | 9/2002 | Burmeister et al. | |
| 6,458,137 B1 | 10/2002 | Klint | |
| 6,547,815 B2 | 4/2003 | Myers | |
| 6,554,849 B1 | 4/2003 | Jones et al. | |
| 6,572,650 B1 | 6/2003 | Abraham et al. | |
| 6,616,680 B1 | 9/2003 | Thielen | |
| 6,656,206 B2 | 12/2003 | Corcoran et al. | |
| 6,673,100 B2 * | 1/2004 | Diaz et al. | 623/1.11 |
| 6,752,826 B2 | 6/2004 | Holloway et al. | |
| 6,790,218 B2 | 9/2004 | Jayaraman | |
| 6,939,361 B1 * | 9/2005 | Kleshinski | 606/200 |
| 6,939,377 B2 | 9/2005 | Jayaramann et al. | |
| 6,994,092 B2 | 2/2006 | van der Burg et al. | |
| 6,994,717 B2 | 2/2006 | Kónya et al. | |
| 7,101,395 B2 | 9/2006 | Tremulis et al. | |
| 7,261,731 B2 * | 8/2007 | Patel et al. | 623/1.15 |
| 2001/0025187 A1 | 9/2001 | Okada | |
| 2001/0039450 A1 | 11/2001 | Pavcnik et al. | |
| 2002/0029051 A1 | 3/2002 | Callister et al. | |
| 2002/0038151 A1 | 3/2002 | Plouhar et al. | |
| 2002/0111647 A1 | 8/2002 | Khairkhahan et al. | |
| 2002/0187288 A1 | 12/2002 | Lim et al. | |
| 2002/0198563 A1 | 12/2002 | Gainor et al. | |
| 2003/0028213 A1 * | 2/2003 | Thill et al. | 606/200 |
| 2003/0051735 A1 | 3/2003 | Pavcnik et al. | |
| 2003/0057156 A1 | 3/2003 | Peterson et al. | |
| 2003/0093108 A1 * | 5/2003 | Avellanet et al. | 606/194 |
| 2003/0139819 A1 | 7/2003 | Beer et al. | |
| 2003/0144694 A1 | 7/2003 | Chanduszuko et al. | |
| 2003/0149471 A1 | 8/2003 | Brianna et al. | |
| 2003/0191495 A1 | 10/2003 | Ryan et al. | |
| 2003/0206860 A1 | 11/2003 | Bleyer et al. | |
| 2004/0073242 A1 | 4/2004 | Chanduszko | |
| 2004/0087999 A1 | 5/2004 | Bosma et al. | |
| 2004/0093017 A1 | 5/2004 | Chanduszko | |
| 2004/0098030 A1 | 5/2004 | Makower et al. | |
| 2004/0098042 A1 * | 5/2004 | Devellian et al. | 606/213 |
| 2004/0143277 A1 | 7/2004 | Marino et al. | |
| 2004/0143293 A1 * | 7/2004 | Marino et al. | 606/213 |
| 2004/0166169 A1 | 8/2004 | Malaviya et al. | |
| 2004/0176799 A1 * | 9/2004 | Chanduszko et al. | 606/213 |
| 2004/0213756 A1 | 10/2004 | Michal et al. | |
| 2004/0220610 A1 | 11/2004 | Kreidler et al. | |
| 2004/0225324 A1 | 11/2004 | Marino et al. | |
| 2005/0043759 A1 | 2/2005 | Chanduszko | |
| 2005/0049668 A1 * | 3/2005 | Jones et al. | 623/1.12 |
| 2005/0070794 A1 | 3/2005 | Deal et al. | |
| 2005/0070821 A1 | 3/2005 | Deal et al. | |
| 2005/0085843 A1 * | 4/2005 | Opolski et al. | 606/191 |
| 2005/0125050 A1 | 6/2005 | Carter et al. | |
| 2005/0154252 A1 | 7/2005 | Sharkey et al. | |
| 2005/0203568 A1 | 9/2005 | Burg et al. | |
| 2005/0222604 A1 * | 10/2005 | Schaeffer | 606/200 |
| 2005/0228434 A1 | 10/2005 | Amplatz et al. | |
| 2005/0249772 A1 | 11/2005 | Malaviya et al. | |
| 2005/0256532 A1 | 11/2005 | Nayak et al. | |
| 2005/0267524 A1 | 12/2005 | Chanduszko | |
| 2005/0273124 A1 | 12/2005 | Chanduszko | |
| 2005/0273135 A1 | 12/2005 | Chanduszko et al. | |
| 2005/0288706 A1 | 12/2005 | Widomski et al. | |
| 2005/0288786 A1 | 12/2005 | Chanduszko | |
| 2006/0009799 A1 * | 1/2006 | Kleshinski et al. | 606/200 |
| 2006/0009800 A1 | 1/2006 | Christianson et al. | |
| 2006/0014998 A1 * | 1/2006 | Sharkey et al. | 600/16 |
| 2006/0030881 A1 | 2/2006 | Sharkey et al. | |
| 2006/0052816 A1 | 3/2006 | Bates et al. | |
| 2006/0106420 A1 | 5/2006 | Dolan et al. | |
| 2006/0201996 A1 | 9/2006 | Hodde | |
| 2006/0210603 A1 | 9/2006 | Williams et al. | |
| 2006/0216326 A1 | 9/2006 | Pacetti | |
| 2006/0235463 A1 | 10/2006 | Freudenthal et al. | |
| 2006/0271030 A1 | 11/2006 | Francis et al. | |
| 2007/0038241 A1 * | 2/2007 | Pal | 606/200 |
| 2007/0179527 A1 | 8/2007 | Eskuri et al. | |
| 2008/0302368 A1 * | 12/2008 | McGuckin et al. | 128/831 |

OTHER PUBLICATIONS

Christian Jux, M.D. et al., A New Biological Matrix for Septal Occlusion, Journal of Interventional Cardiology, vol. 16, No. 2, pp. 149-152, 2003.

Christian Jux, M.D. et al., Interventional Atrial Septal Defect Closure Using a Totally Bioresorbable Occluder Matrix, Journal of the American College of Cardiology, vol. 48, No. 1, pp. 161-169, 2006.

Amplatz Vacular Obstruction Device, Cook Medical Inc., 4pp., 2005.

\* cited by examiner

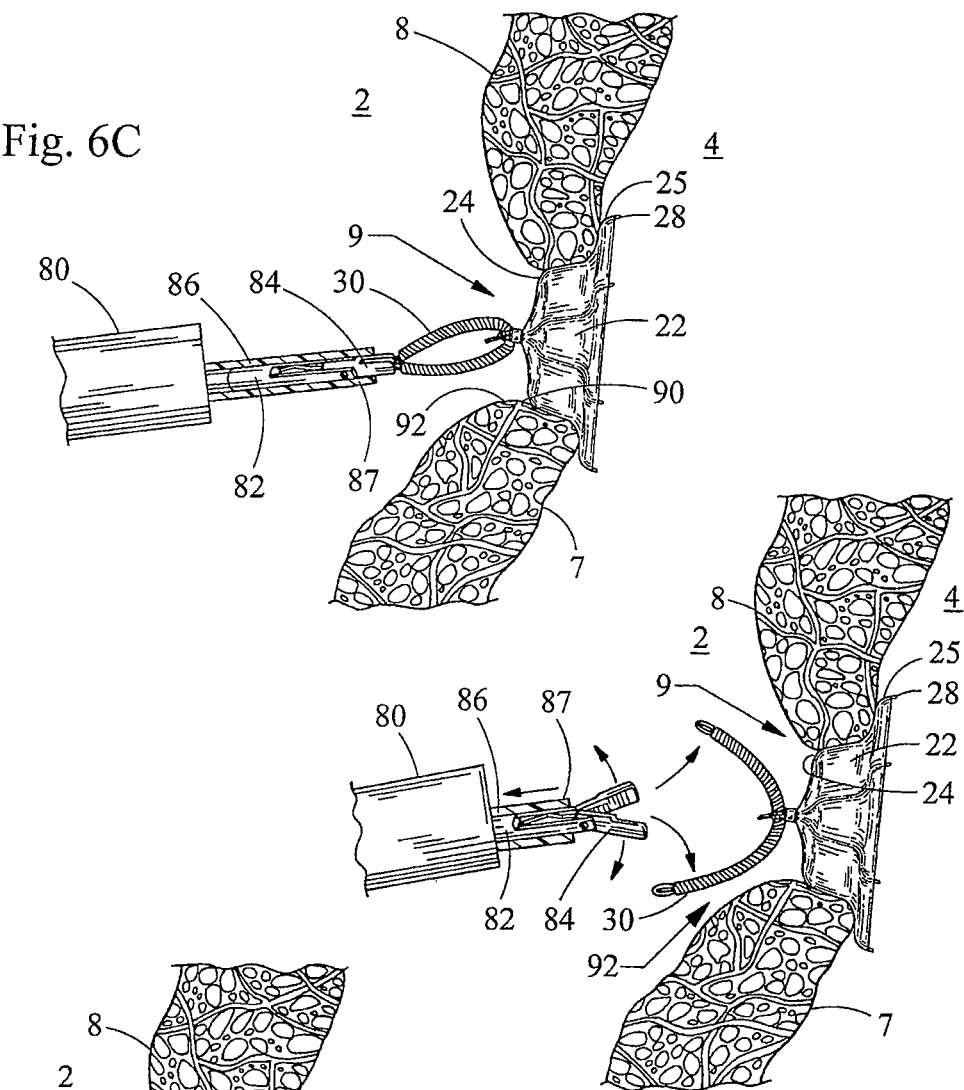

SPIDER PFO CLOSURE DEVICE

BACKGROUND

A patent foramen ovale (PFO) is a persistent, one-way, usually flap-like opening in the wall between the right atrium and left atrium of the heart. In utero, the foramen ovale serves as a physiologic conduit for right-to-left shunting of blood in the fetal heart. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure presses the septum primum against the walls of the septum secundum, covering the foramen ovale and resulting in functional closure of the foramen ovale. This closure is usually followed by anatomical closure of the foramen ovale due to fusion of the septum primum to the septum secundum.

Where anatomical closure of the foramen ovale does not occur, a PFO is created. Studies have shown that a relatively large percentage of adults have a PFO. The presence of a PFO is generally considered to have no therapeutic consequence in otherwise healthy adults. Because left atrial (LA) pressure is normally higher than right atrial (RA) pressure, the flap usually stays closed. Under certain conditions, however, right atrial pressure can exceed left atrial pressure, creating the possibility that blood could pass from the right atrium to the left atrium and blood clots could enter the systemic circulation. It is desirable that this circumstance be eliminated.

Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. It has been estimated that in 50% of cryptogenic strokes, a PFO is present. In addition, there is significant evidence that patients with a PFO who have had a cerebral vascular event are at increased risk for future, recurrent cerebrovascular events.

Patients suffering a cryptogenic stroke or a transient ischemic attack (TIA) in the presence of a PFO often are considered for medical therapy to reduce the risk of a recurrent embolic event. Accordingly, patients at such an increased risk are considered for prophylactic medical therapy to reduce the risk of a recurrent embolic event. These patients are commonly treated with oral anticoagulants to reduce the risk of a recurrent embolic event. However, these anticoagulants have potentially adverse side effects, including hemorrhaging, hematoma, and adverse interactions with other drugs. In addition, use of anticoagulant drugs can alter a person's recovery and necessitate adjustments in a person's daily living pattern.

Where anticoagulation is contraindicated, surgery may be employed to close a PFO. The surgery would typically include suturing a PFO closed by attaching septum secundum to septum primum. Like other open surgical treatments, however, this surgery is highly invasive, risky, requires general anesthesia, and may result in lengthy recuperation.

Nonsurgical closure of PFOs has become possible with the introduction various mechanical closure devices, including umbrella devices and the like, which were initially for percutaneous closure of atrial septal defects (ASDs; a condition where there is not a septum primum). These devices potentially allow patients to avoid the side effects often associated with anticoagulation therapies and the risks of invasive surgery.

However, devices for treating heart defects, such as PFO and other atrial and ventricular septal heart defects have their share of drawbacks. The complex anatomical features of PFOs present a challenge to a one size fits all approach. The PFO involves two components, septum primum and septum secundum. The septum secundum is thicker than septum primum and exhibits limited mobility and compliance. Failure of these two structures to fuse creates a tunnel-like passageway, the PFO. The distance of the nonfusion between the two septa determines the particular size of the PFO, which must be considered in the design of a device targeting PFOs. Nevertheless, devices are often configured so that the patient's anatomy must be adjusted to fit the geometry of the device. As a consequence, heart tissue may be torn when accommodating such devices.

Conventional nonsurgical closure devices are often technically complex, bulky, have a high septal profile, low radiopacity, and an inability to provide immediate closure. Additionally, many of the devices have a geometry which tends to prevent the device from remaining flat against, or within the defect once deployed. The varying passageway geometries often require multiple sized devices. Moreover, many devices are set apart by a relatively long central section corresponding to the PFO tunnel. By increasing the device profile, the device can present difficulties with respect to complete endothelialization. Conventional closure devices are often difficult to deploy or reposition, often require replacement or repositioning, and require relatively large delivery catheters (for example, 9-10 French or more). In addition, the large masses of foreign material associated with the device may lead to unfavorable body adaptation to the device, including thromboses or other unfavorable reactions. Further drawbacks to nonsurgical closure devices include complications resulting from fractures of the components, conduction system disturbances, perforations of heart tissue, residual leaks, and inability to allow subsequent methods involving transeptal puncturing.

Accordingly, there is a need for improved low profile closure devices and simplified delivery methods for improved closure, which are capable of limiting the amount of foreign material deployed and enhancing closure stability. The present invention is designed to address a number of the deficiencies surrounding conventional closure devices.

SUMMARY

In one aspect, a closure device for closing or occluding bodily passageways, including septal openings, such as PFOs, includes an occluding body formed from a plurality of flexible outwardly radiating occluding wires connected to or covered by biocompatible sheet materials, including bioremodelable sheet materials. The occluding wires are joined together at proximal wire ends. Linking members connectively link the occluding body to a flexible, substantially linear anchor structure formed from at least one tube, coil, or bar. The anchor may be configured for placement on one side of bodily passageway, whereby the longitudinal axis of at least one anchor extends across a transverse cross-section of the bodily passageway, anchoring the occluding body in place against the other side of a bodily passageway to close, occlude, or fill at least a lumenal portion of a bodily passageway.

The occluding body includes a plurality of flexible outwardly radiating occluding wires, which are preferably configured in a deployed configuration to be inwardly biased against tissues surrounding a bodily passageway, such as a PFO. The occluding wires may be inwardly biased against the tissue portions in a bodily passageway, as well as tissue portions surrounding an end of the bodily passageway. The occluding wires may be joined together at proximal wire ends. A clamp may be used to secure the proximal wire ends.

The anchor includes a tube, coil, or bar, which can include or be connected to a grasping member having a structural configuration for releasable attachment to an anchor engaging member facilitating delivery of the closure device. The anchor may include a coil with an anchor wire extending longitudinally therethrough, whereby the anchor wire includes one or more terminally disposed grasping members. The grasping member(s) may include a loop structure or other suitable structure for releasable attachment to an anchor engaging member facilitating delivery of the closure device. The loop structure may be formed from a wire extending through a coil and frictionally engaged therefrom.

In another aspect, a closure device assembly and method for delivering the closure device includes a delivery catheter containing a pre-loaded closure device collapsibly disposed at a terminal end. An anchor in the closure device is connected to an anchor engaging member, such as biopsy forceps. The anchor may include one or more terminally disposed grasping member(s), which are connected to the anchor engaging member. The anchor engaging member may be contained in a smaller coaxially disposed locking catheter, which is configured to prevent inadvertent release of the closure device when held in a compressed state inside the delivery catheter. Advancement of the anchor engagement member and/or retraction of the locking catheter sheath disengages (and releases) the closure device from the anchor engaging member near a site proximal to a septal defect, such as a PFO. Upon release of the device (or anchor) from the anchor engaging member, portions of the occluding body and anchor are co-localized on opposite sides of the bodily passageway, thereby securing the closure device to close or occlude the bodily passageway. In a preferred embodiment, a closure device or assembly is used to in a method for closing a bodily passageway, including a septal opening, such as a PFO.

BRIEF DESCRIPTION OF THE DRAWINGS

FIG. 3A shows another occluding body embodiment without the biocompatible sheet materials or clamp.

FIG. 6C shows a cross-sectional view of the distal end of the closure device assembly of FIG. 5B showing disengagement of the anchor from a biopsy forceps.

FIG. 6D-E shows a cross-sectional view illustrating a deployed closure device closing a PFO.

DETAILED DESCRIPTION

Figure 1:
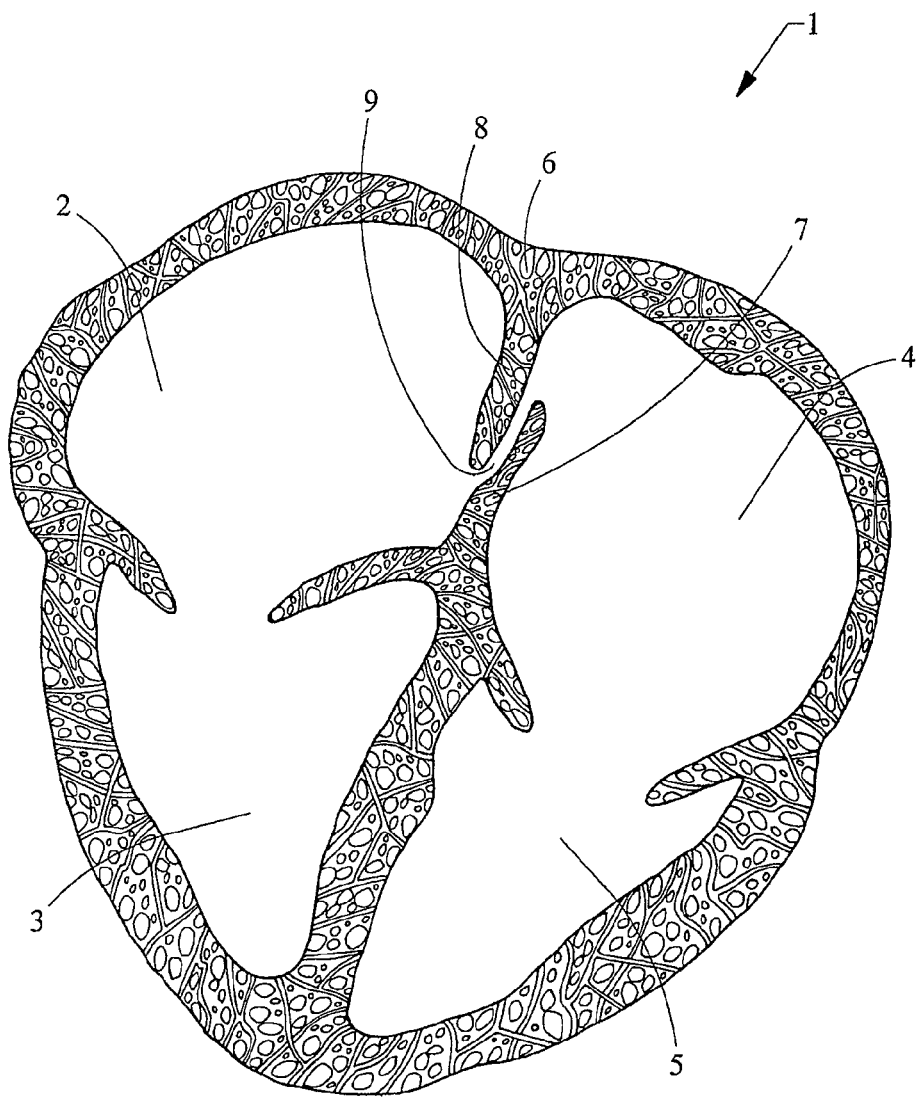
FIG. 1 shows a cross-sectional view of a heart with a PFO.

A closure device for closing or occluding bodily passageways, including septal openings of the heart is provided. Without wishing to be bound by a particular theory or to in any way limit the scope of the appended claims and their equivalents, it is believed that incorporation of bioremodelable material capable of causing angiogenesis and replacement by host tissues according to the present invention provides a more stable and permanent closure, thereby addressing one or more limitations associated with conventional closure devices.

In order to provide a clear and consistent understanding of the specification and claims, the following definitions are provided.

As used herein, the terms "opening", "bodily opening", "passageway", and "bodily passageway" are interchangeably used to refer to a bodily opening, aperture, canal, conduit, or duct, including but not limited to septal openings, PFOs, heart valves, blood vessels, vessel punctures, bile ducts, and the like.

The term "connected" refers to the joining, adhering, bonding, attaching, or the like, of two elements. Two elements will be considered to be connected together when they are connected directly to one another or indirectly to one another, such as when each is directly connected to intermediate elements.

The term "anchor" refers to a flexible, substantially linear structure having a longitudinal axis which is configured to extend across a transverse cross-section of a bodily passageway, anchoring an occluding body into a bodily passageway.

The term "grasping member" refers to a grasping structure on an anchor having a shape suitable (for example, loop, knob, ball, hook, and the like) for releasable attachment to an anchor engaging member. The grasping member may be integral to a tube, coil or bar in an anchor or it may be disposed on a second structure separate from and connected to the tube, coil or bar.

The term "anchor engaging member" refers to a member facilitating delivery of the closure device by releasable attachment to at least one anchor by way of one or more grasping members.

The term "anchor engagement portion" refers to a portion of the anchor engaging member having a complementary structure configured for linkage and releasable attachment to the grasping member.

As used herein, the term "biocompatible" refers to a material that is substantially non-toxic in the in vivo environment of its intended use, and that is not substantially rejected by the patient's physiological system or is non-antigenic. This can be gauged by the ability of a material to pass the biocompatibility tests set forth in International Standards Organization (ISO) Standard No. 10993; the U.S. Pharmacopeia (USP) 23; or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, immunogenicity, and combinations thereof. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

As used herein, the term "bioresorbable" refers to refers to those materials of either synthetic or natural origin which, when placed in a living body, are degraded through either enzymatic, hydrolytic or other chemical reactions or cellular processes into by-products which are either integrated into, or expelled from, the body. It is recognized that in the literature, the terms "resorbable", "absorbable", and "bioabsorbable" are frequently used interchangeably.

As used herein, the term "bioremodelable" refers to a natural or synthetic material that is bioresorbable and capable of inducing angiogenesis, tissue remodeling, or both in a subject or host. A bioremodelable material includes at least one bioactive agent capable of inducing angiogenesis or tissue remodeling. The bioactive agent(s) in the bioremodelable material may stimulate infiltration of native cells into an acellular matrix, and formation of new blood vessels (capillaries) growing into the matrix to nourish the infiltrating cells (angiogenesis). Additionally, the bioactive agent(s) may effect the degradation or replacement of the bioremodelable material by endogenous tissue. The bioremodelable material may include a naturally derived collagenous extracellular matrix (ECM) tissue structure present in, for example, native submucosal tissue sources, including, but not limited to small intestine submucosal (SIS) tissue, or it may include any one of a variety of different non-submucosal ECM-containing tissue materials or synthetic, bioresorbable non-ECM materials capable of inducing angiogenesis and tissue remodeling in a host.

The phrases "sheet of biocompatible material" and "sheet of bioremodelable material" refer to one or more biocompatible or bioremodelable tissue layers or synthetic polymeric layers formed into a sheet or composite thereof. A sheet of biocompatible or bioremodelable material may include, for example, extracellular matrix tissue, including one or more naturally-derived tissue layers containing an ECM scaffold, one or more biocompatible polymeric layers, or combinations thereof. The sheet of biocompatible or bioremodelable material can be in the form of a single tissue or polymeric layer or a plurality of tissue or polymeric layers in form of laminates, composites, or combinations thereof.

The terms "angiogenesis" and "angiogenic" refer to bioactive properties, which may be conferred by a bioremodelable material through the presence of growth factors and the like, which are defined by formation of capillaries or microvessels from existing vasculature in a process necessary for tissue growth, where the microvessels provide transport of oxygen and nutrients to the developing tissues and remove waste products.

The term "submucosa" refers to a natural collagen-containing tissue structure removed from a variety of sources including the alimentary, respiratory, intestinal, urinary or genital tracts of warm-blooded vertebrates. Submucosal material according to the present invention includes tunica submucosa, but may include additionally adjacent layers, such the lamina muscularis mucosa and the stratum compactum. A submucosal material may be a decellularized or acellular tissue, which means it is devoid of intact viable cells, although some cell components may remain in the tissue following purification from a natural source. Alternative embodiments (for example, fluidized compositions and the like) include submucosal material expressly derived from a purified submucosal matrix structure. Submucosal materials according to the present disclosure are distinguished from collagen materials in other closure devices that do not retain their native submucosal structures or that were not prepared from purified submucosal starting materials first removed from a natural submucosal tissue source.

The term "small intestinal submucosa" (SIS) refers to a particular submucosal tissue structure removed from a small intestine source, such as pig.

The term "radiopaque" refers to a non-toxic material capable of being monitored or detected during injection into a mammalian subject by, for example, radiography or fluoroscopy. The radiopaque material may be either water soluble or water insoluble. Examples of water soluble radiopaque materials include metrizamide, iopamidol, iothalamate sodium, iodomide sodium, and meglumine. Examples of water insoluble radiopaque materials include tantalum, tantalum oxide, and barium sulfate, which are commercially available in the proper form for in vivo use. Other water insoluble radiopaque materials include, but are not limited to, gold, tungsten, stainless steel, and platinum.

FIG. 1 is a schematic front view of a heart 2 with a septal defect, such as patent foramen ovale (PFO). The heart 1 has a right atrium 2, right ventricle 3, left atrium 4, and a left ventricle 5. The septum 6 between the right atrium 2 and the left atrium 4 comprises a septum primum 7 and a septum secundum 8. The PFO 9 is a passageway in the septum 6 that has not properly closed. Where a PFO 9 is present, the septum primum 7 typically overlaps the septum secundum 8 and the higher pressure in the left atrium 4 typically closes the flaps of the septum primum 7 and the septum secundum 8 so that blood does not leak between the atria 2 and 4. However, when there is a pressure change in the chest, the flaps may separate permitting blood to flow through the PFO and between the atria 2 and 4.

Figure 2A:
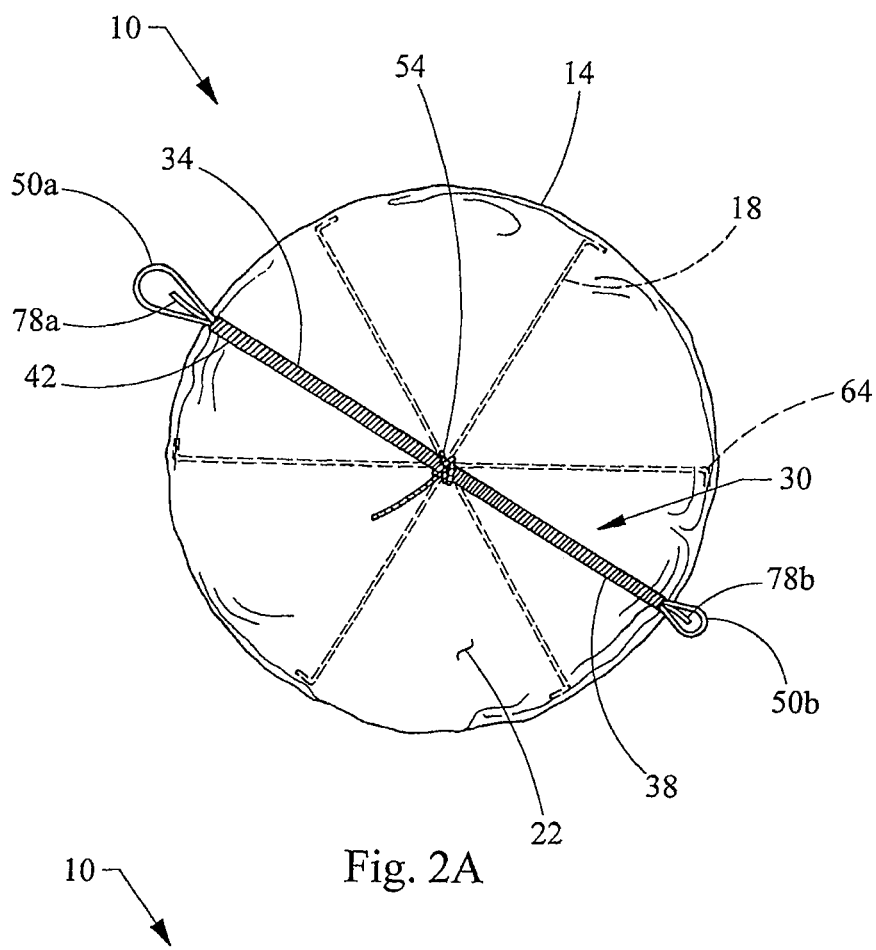
FIG. 2A shows a plan view of an exemplary closure device according to an embodiment of the present invention.
Figure 2B:
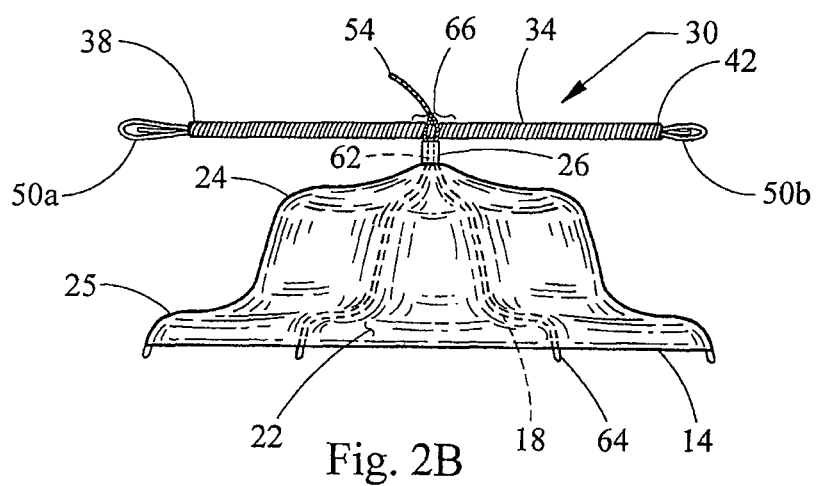
FIG. 2B shows a side view of an exemplary closure device according to an embodiment of the present invention.

FIGS. 2A and 2B depict an exemplary closure device 10 according to several aspects of the present invention. The closure device 10 includes an occluding body 14 formed from a plurality of flexible outwardly radiating occluding wires 18 connected to or covered by one or more biocompatible sheet materials 22. Preferably, the biocompatible sheet materials 22 include bioremodelable sheet materials, such as collagenous ECM materials. The occluding body 14 is connected to one or more anchor(s) 30 by one or more linking member(s) 54 (depicted as sutures). The anchor(s) 30 may be configured for placement on a proximal side of a bodily passageway, to anchor distal occluding wire end portions against a distal side of a bodily passageway and/or to anchor the occluding body 14 into the bodily passageway to close, occlude, or fill at least a lumenal portion of a bodily passageway.

The occluding body 14 includes a plurality of flexible outwardly radiating occluding wires 18 connected to or covered by one or more biocompatible sheet materials 22. The occluding wires 18 are joined together at proximal wire ends. A clamp 26 may be used to secure the proximal wire ends. Proximal occluding wire 18 ends may be housed in a central bore 62 contained within a clamp 26.

Figure 3A:
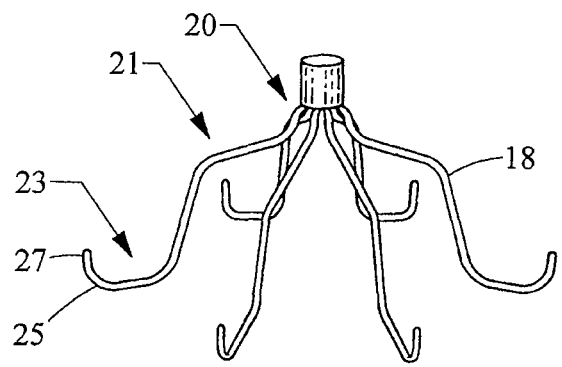
FIG. 3A shows an occluding body embodiment without the biocompatible sheet materials or clamp.
Figure 3B:
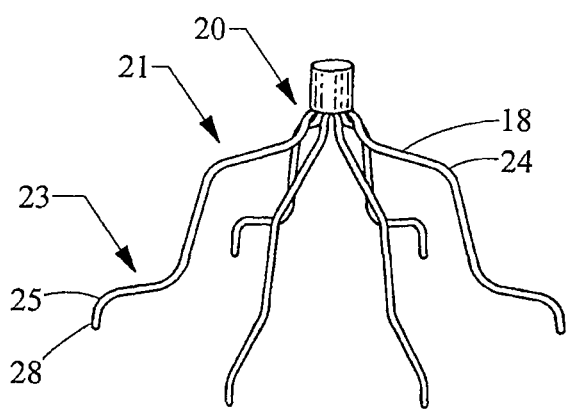

FIGS. 3A and 3B depict an occluding body 14 without the biocompatible sheet 22 materials or the clamp 26. Six outwardly radiating occluding wires 18 of the occluding body 14 form a spider-like skeleton structure for attachment to the biocompatible sheet materials 22. Any number of occluding wires 18 suitable for forming a skeleton capable of supporting the biocompatible sheet material 22 for occlusion of a bodily passageway 9 may be used. In FIGS. 3A and 3B, occluding wires 18 are joined together at proximal wire ends 20. Whereas proximal occluding wire portions 23 are configured for placement inside a bodily passageway 9, distal occluding wire portions 24 are configured for placement outside the bodily passageway 9 to aid in anchoring the closure device 10 to the distal end 90 of the bodily passageway as depicted in FIG. 6E. Thus, where a clamp 26 is used to secure the proximal wire ends, the clamp 26 is generally configured to be partially or completely disposed within the bodily passageway 9 following deployment of the closure device 10.

The occluding wires 18 are preferably configured in an expanded, deployed configuration to maximize contact between the biocompatible sheet materials 22 and tissue portions surrounding a bodily passageway 9, such as a PFO. Accordingly, as depicted in FIG. 3B, proximal occluding wire portions 23 may have an arcuate conformation in which proximal occluding wire portions 23 configured for placement inside a bodily passageway are outwardly biased against internal bodily passageway portions adjacent to a proximal end 92 of a bodily passageway 9. Alternatively, or in addition, the distal occluding wire portions 24 may have an arcuate conformation in which the distal occluding wire portions 24 configured for placement outside a bodily passageway 9 at a position adjacent to a distal passageway end 90 are inwardly biased against tissue portions surrounding the distal end 90 of the bodily passageway 9 (FIGS. 3A and 3B).

More particularly, one or more of the outwardly radiating occluding wires 18 may be configured with one or more bend portion(s) 24, 25 biasing the occluding wires 18 against tissue portions surrounding a bodily passageway 9. For example, FIG. 3B depicts a first bend portion 24, which is configured to outwardly bias proximal occluding wire portions 23 against tissue portions within a bodily passageway 9 toward a proximal end 92. FIGS. 3A and 3B depict a second bend portion 25, which is configured to inwardly bias distal occluding wire portions 23 against tissue portions outside the bodily passageway 9 surrounding the distal end 90 of the bodily passageway 9. The bend portions 24, 25 are configured to help anchor the occluding body 14 into the bodily passageway.

In addition, as depicted in FIG. 3A, proximal to the second bend portion 25, the distal occluding wire portions 23 may further include a terminal end portion 27 extending inward, engaging or gripping the surrounding tissues during deployment. An inwardly extending terminal end portion 27 may form a bend angle with the second bend portion 25 greater than 90°, but less than 180°. Alternatively, the distal occluding wire portions 23 may include a terminal end portion 28 extending upward, away from the surrounding tissues as depicted in FIG. 3B.

Biocompatible sheet material 22 may be attached underneath the spider-like skeleton, over the spider-like skeleton, or combinations thereof. The occluding wires 18 may extend through the biocompatible sheet material 22 at one end. The biocompatible sheet material 22 may be attached by any suitable attachment method known to those of skill in the art. Biocompatible or bioremodelable sheet materials 22 may be attached either side of the occluding wires 18, or both.

Biocompatible or bioremodelable sheet materials 22 may be attached to the occluding wires 18 by any suitable attachment method. In one aspect, the biocompatible of bioremodelable sheet material(s) (or composites thereof may be attached by sutures 54. Alternative attachment methods include, but are not limited to, use of biological adhesives, use of chemical cross-linking agents, crimping, tissue welding, heat welding, pressure welding, heat source, light source, radiofrequency, lasering, other energy sources, and the like. Methods for attaching sheet materials to wires or wired frames are described in U.S. Patent Application Publication No. 2001/0039450 A1, the disclosures of which are expressly incorporated by reference herein.

Because the sheet material 22 is configured to completely cover a bodily passageway, the sheet material 22 and occluding wires 18 will have a diameter in a deployed state that is larger than the diameter of the passageway for occlusion. Thus, when deployed, the sheet material 22 may have a diameter between about 5 to about 50 mm, preferably between about 9 to about 30 mm. Similarly, the occluding wires 18 may be configured in a deployed state whereby the diameter between opposite wire bends 20 is between about 5 to about 50 mm, preferably between about 9 to about 30 mm.

In a particular embodiment, biocompatible sheet material 22 is attached to an Amplatz Vascular Obstruction Device (Cook Medical Inc., Bloomington, Ind.) or a modified version thereof. The Amplatz Vascular Obstruction Device has a stainless steel construction, including six outwardly radiating wires in a spider-like configuration linked to a clamp. The Amplatz Device is available in diameter sizes ranging from 9-20 mm. The outwardly radiating wires include a bend portion toward their distal ends with tips extending upward, forming a bend angle greater than 90°, but less than 180°.

The Amplatz Vascular Obstruction Device is typically used to prevent dislodgement of embolization coils and is configured for delivery through a catheter or introducer sheath having an inner diameter sheath size between 0.068 inches and 0.080 inches. Accordingly, an Amplatz Vascular Obstruction Device covered with biocompatible sheet material and linked to a flexible anchor can be delivered using small delivery catheters, including a 5 French Flexor® Introducer (Cook Medical Inc., Bloomington, Ind.) having an inner sheath diameter size of 0.074 inches.

The occluding body 14 is connected to one or more anchor(s). An anchor 30 is defined by a flexible, substantially linear structure having two ends, which is configured to extend across a transverse cross-section of a bodily passageway so as to anchor an occluding body into a bodily passageway. The anchor 30 may be configured to include a coil, bar, cylinder, or tube having two ends and a circular, elliptical or polygonal cross-sectional shape. When utilizing a bar, cylinder, or tube in an anchor 30, the bar, cylinder, or tube may solid or hollow in nature.

The anchor 30 is preferably configured for placement on a side of a bodily passageway to anchor distal occluding wires against one side of a bodily passageway and to position proximal occluding wire ends inside the bodily passageway. The anchor(s) 30 are connected to the occluding body 14 so that in a deployed state, the longitudinal axis of at least one anchor 30 is substantially perpendicular to the longitudinal axis of the bodily passageway. Preferably, the anchor(s) 30 are joined to the occluding body 14 to permit rotation of the anchor(s) 30 relative to the occluding body 14 or the longitudinal axis of the bodily passageway.

Figure 4:
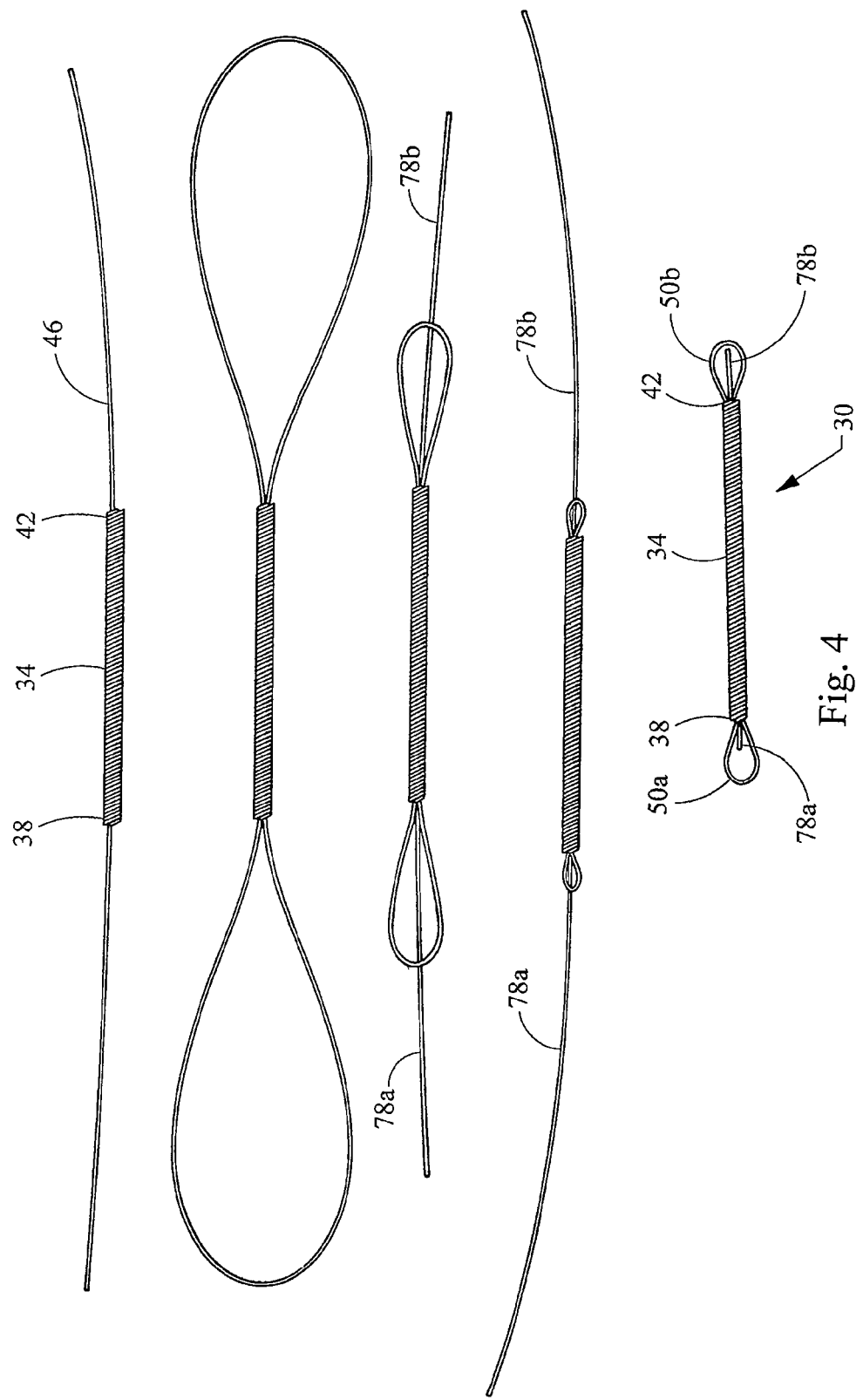
FIG. 4 shows a method for forming an anchor structure according to an aspect of the present invention.

An anchor 30 may include one or more grasping member(s) having a suitable structure for releasable attachment to an anchor engaging member facilitating delivery of the closure device. FIGS. 2A and 2B depict an exemplary anchor in the form of a linear coil connected to two terminally disposed grasping members 50a, 50b, which are configured for releasable attachment to an anchor engaging member 82 as depicted in FIGS. 4 and 5 below. The grasping member 50 may be disposed on or connected to the anchor 30 at any suitable site. An anchor 30 may include one or more grasping member(s) 50 having structures integral or separate from the tube, coil, or bar. Preferably, the anchor 30 includes or is connected to one or more terminally disposed grasping member(s) 50.

An anchor engaging member facilitates delivery of the closure device 10. The anchor engaging member includes an anchor engagement portion having a structure complementary to the grasping member 50, and is configured for releasable attachment thereto. In a preferred embodiment, the anchor engaging member 82 includes biopsy forceps. The anchor engagement portion 84 may include a ball, hook, loop, pair of cups or jaws, or any other suitable member capable of releasable attachment to a grasping member 50.

In FIGS. 2A and 2B, the terminally disposed loop structures 50a, 50b are formed from an anchor wire extending through the coil 34 three times to form terminally disposed loop structures 50, which are frictionally engaged by the anchor coil 34 at both anchor coil ends 38, 42. In this embodiment, the anchor 30 is defined by a first end 38 and a second end 42, whereby the grasping member(s) 50a, 50b constitute structures separate from that of the anchor coil 34, which are configured for releasable attachment to an anchor engaging member 82

Generally at least one anchor 30 in the closure device 10 of the present invention includes or is connected to at least one grasping member 50. The grasping member 50 includes a grasping structure having a shape suitable (for example, loop, knob, ball, hook, and the like) for releasable attachment to an anchor engaging member facilitating delivery of the closure device 10. The grasping member 50 may be integral to the tube, coil, or bar, or it may include a separate structure connected to the tube, coil, or bar. The grasping member 50 may be positioned at any anchor 30 site suitable for delivery of the closure device 10.

FIG. 4 depicts a process for forming an anchor 30 containing terminally disposed loop structures 50a, 50b proximal to each coil end 38, 42 in which an anchor wire 46 is passed through a coil 34 three times. The loop structures 50 may be formed by extending an anchor wire 46 through the coil 34, looping the anchor wire 46 back towards each open coil end 38, 42, pulling the anchor wire 46 at each coil end 38, 42 back through the coil 34 in the opposite direction to achieve a desired loop size, and cutting off the excess free ends 78a, 78b extending from each coil end 38, 42. The free ends 78a, 78b may be looped back, knotted, crimped, or welded together near the coil ends 38, 42 to stabilize the terminally disposed loop structures 50a, 50b proximal to each coil end 38, 42. By configuring the loop structures 50 to be wider than the coil 34 diameter at each coil end 38, 42, the grasping members or loop structures 50a, 50b are frictionally engaged and/or secured by the coil 34. Accordingly, grasping member(s) 50 may comprise structure(s) separate from that of a coil 34 (or other hollow tubular variant thereof).

Grasping member(s) 50 can be formulated to include virtually any graspable structure having a complementary shape suitable (for example, knob, ball, hook, and the like) for releasable attachment to an anchor engaging member facilitating delivery of the closure device 10. Grasping member(s) 50 may be integrally formed from the tube, coil, or bar used to form the anchor 30. Alternatively, the grasping member(s) 50 may be formed from secondary materials, for example, wires longitudinally extending through a coil, hollow tube, or hollow bar. In this case, the grasping member(s) may be terminally disposed structures frictionally engaged by a coil or otherwise hollow member (as described above). Additionally, the grasping member(s) 50 may be directly attached or linked to a tube, coil, or bar by any suitable attachment method known to those of skill in the art. For example, the grasping member(s) 50 may be attached using wires, threaded materials, sutures, or adhesives, or they may be soldered or welded to a tube, coil, or bar. In addition, the grasping member(s) 50 may be attached using structures capable of being interlinked with structures associated with the tube, coil, or bar.

The anchor 30 may be variably sized depending on the size of the bodily passageway or septal opening, such as a PFO. Generally, the anchor 30 is configured to overlap and become stably secured over the opening at one end of the bodily passageway opposite the opening occluded by the occluding body 14. The anchor 30 and the occluding body 14 are therefore configured to be sandwiched around the two openings defining the bodily passageway. The length of the anchor 30 can be modified depending on the size of the opening. Thus, the anchor may have a length between about 5 to about 50 mm, preferably between about 15 to about 30 mm. Similarly the length of the occluding wires 18, clamp 26, and/or linking member(s) 54 may be modified depending on the length of the bodily passageway for occlusion.

The occluding body 14 is connected to one or more anchor(s) 30 though one or more linking member(s) 54. The linking members 54 may include sutures, wires or other suitable linking structures known to those of skill in the art. Linking members may extend through one or more portions of the occluding body 14. In FIG. 2A, a linking member 54 is depicted as a suture extending through the central bore 62 in the clamp 26, whereby the suture 54 connectively links the occluding body 14 to the anchor 30. Similarly, one or more wire(s) could be used to link the occluding body 14 to the anchor 30. For example, the wire(s) may be attached to the anchor 30, clamp 26, or both, by tying, crimping, welding, soldering, combinations thereof, or any other attachment method known to those of skill in the art. A plurality of anchors 30 may be connected to the occluding body 14 for additional anchoring or support. Depending on the length of the bodily passageway for occlusion, as well as the length and configuration of the occluding wires 18, the occluding body 14 may be spaced from the anchor(s) 30 at a sufficient distance to facilitate stable anchoring of the occluding body 14 by the anchor(s).

To facilitate the joining of the anchor(s) 30 to the occluding body 14, a center region 66 in an anchor coil 34 may be partially stretched to create interrupted regions or grooves (not shown) facilitating more secure linkages between the linking member(s) 54 and an anchor coil 34. In particular, linking members 54 in the form of wires or sutures can wrap around and become more securely engaged by the groove areas when connecting the anchor(s) 30 to the clamp 26.

A closure device 10 of the present invention is made of flexible materials to facilitate collapsible retention and delivery from a variety of delivery catheter sizes, including 5, 6, 7, or 8 French size delivery catheters having an inner sheath diameter between 0.074 inches and 0.113 inches. Accordingly, one or more of the component device parts of the closure device 10 may be made from flexible and/or shape memory alloy materials, such as Nitinol, including those described in U.S. Pat. Nos. 4,665,906, 5,108,420. In particular, Shape-memory materials may be included in a number of component device 10 parts, including, but not limited to the occluding body 14, occluding wires 18, clamp 26, anchor 30, coil 34, anchor wire 46, and grasping members 50. Preferably, the occluding wires 18 and the anchor wires 46 are made from or include shape memory alloy material(s). In a preferred embodiment, the occluding wires 18 and the anchor wires 46 are made of Nitinol.

Shape-memory materials, including Nitinol alloys, may be utilized whereby the alloy material(s) is compressed or partially expanded in its martensitic state and fully expanded in its austenitic state. For example, specific shape memory alloy materials may be chosen so that the closure device 10, including the occluding wires 18, is in the austenitic state at body temperature. Prior to insertion into the body, the closure device 10 may be maintained at a low temperature within the martensitic range. Upon delivery to a desired bodily location, the closure device 10 may be warmed to at least the $A_f$ temperature so that, for example, the occluding wires 18 or anchor(s) 30 expand to their desired configuration.

Suitable shape-memory materials and their use in medical applications are disclosed in U.S. Pat. No. 3,012,882 to Muldawer et al.; U.S. Pat. No. 3,174,851 to Buechler et al.; U.S. Pat. No. 4,665,906 to Jervis; U.S. Pat. No. 5,108,420 to Marks; U.S. Pat. No. 5,769,796 to Palermo et al., U.S. Pat. No. 5,846,247 to Unsworth et al.; and U.S. Pat. No. 6,451,052 to Burmeister et al., the disclosures of which are expressly incorporated herein by reference.

When using sutures as linking members 54 for connectively linking closure device 10 components of the present invention, the sutures 54 may be made from a variety of suture types, including braided or monofilament. Sutures 54 may be made from polyester, polypropylene, polyglycolic acid, polytetrafluoroethylene (PTFE), SIS, nylon, silk or any of a variety of absorbable and non-absorbable suture materials known in the art. The sutures 54 may be treated or coated with radiopaque materials to facilitate visualization of the device by radiography or fluoroscopy. The sutures 54 may also be coated with antibiotics or other antimicrobial agents. Exemplary suture materials include TEVDEK II®, a braided polyester suture material impregnated with PTFE; DEKLENE II®, a polypropylene monofilament suture material, and nylon monofilament suture material, all of which are manufactured by Genzyme Biosurgery of Cambridge, Mass. Preferred suture materials include non-absorbable polypropylene sutures, such as PROLENE™ 6-0 mil (0.1524 mm) diameter (Ethicon Inc., Piscataway, N.J.)

As an alternative to sutures 54, tissue adhesives may be used to link elements of the above disclosed closure device 10 to one another, such as the bioremodelable sheet material 22 to the occluding wires 18. An exemplary tissue adhesive is BioGlue® (CryoLife, Inc.). Other suitable adhesives include fibrin-, fibrinogen-, and thrombin-based sealants, bioactive ceramic-based sealants, and cyanoacrylate sealants, including, but not limited to, Vitex (V.I. Technologies, NY; comprising thrombin:fibrinogen in a 1:1 ratio); Quixil (Omrix Biopharm SA, Brussels); Dermabond, an octylcyanoacrylate tissue adhesive (Bruns and Worthington (2000) Am. Fam. Physician 61:1383-1388); Tisseel (Baxter International, Deerfield, Ill.); Hemaseel APR (Haemacure, Sarasota, Fla.); PlasmaSeal (Plasmaseal, San Francisco, Calif.); AutoSeal (Harvest Technologies, Norwell, Mass.); Floseal (Fusion Medical Technologies, Mountain View, Calif.); and Bioglass (U.S. Biomaterials, Alachua, Fla.); CoStasis (Cohesion Technologies). MedPro Month (1999) 9:261-262; and MedPro Month (2000) 10:86-91.

Bioremodelable Sheet Materials

The closure device includes biocompatible or bioremodelable sheet materials connected to the occluding wires so as to provide a covering, which is suitably configured to close a bodily passageway. When using bioremodelable sheet material as a covering, the bioremodelable sheet material is preferably designed to promote angiogenesis and endothelialization of the implanted closure device. In particular, the bioremodelable sheet material is capable of remodeling the surrounding tissues, such that upon implantation in a patient, the bioremodelable sheet material is degraded and replaced by the patient's endogenous tissues. As the bioremodelable sheet material is remodeled by host tissues, the bodily opening becomes stably closed, obviating concerns about migration of the device.

A bioremodelable sheet material may include one or more bioremodelable tissue layers formed into a sheet. The sheet material may include, for example, a single tissue layer containing ECM material, or it may include additionally adjacent tissue layers or additional tissue layers laminated together in a multilaminate structure. The sheet materials may include or be made from reconstituted or naturally-derived collagenous materials. Preferred bioremodelable materials include naturally derived tissues with ECMs possessing biotropic properties, including in certain forms angiogenic collagenous ECMs. Preferred ECMs include naturally-derived collagenous tissue materials retaining native matrix configurations and bioactive agents, such as growth factors, which serve to facilitate tissue remodeling, as opposed to collagen-based materials formed by separately purifying natural collagen and other associated components away from their native three dimensional matrix configurations or bioactive agents, including growth factors. Suitable collagenous ECMs include those derived from a variety of native tissues, including but not limited to, intestine, stomach, bladder, liver, fascia, skin, artery, vein, pericardium, pleura, heart valve, dura mater, ligament, tendon, bone, cartilage, bladder, liver, including submucosal tissues therefrom, renal capsule membrane, dermal collagen, serosa, mesenterium, peritoneum, mesothelium, various tissue membranes and basement membrane layers, including liver basement membrane, and the like. Suitable submucosa tissue materials for these purposes include, for instance, intestinal submucosa, including small intestinal submucosa, stomach submucosa, urinary bladder submucosa, and uterine submucosa. A particularly preferred ECM material is porcine SIS material. Commercially available ECM materials capable of remodeling to the qualities of its host when implanted in human soft tissues include porcine SIS material (Surgisis® and Oasis® lines of SIS materials, Cook Biotech Inc., West Lafayette, Ind.) and bovine pericardium (Peri-Strips®, Synovis Surgical Innovations, St. Paul, Minn.).

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, and/or protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example, at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material (C. Heeschen et al., Nature Medicine 7 (2001), No. 7, 833-839). When combined with a fluorescence microangiography technique, this model can provide both quantitative and qualitative measures of angiogenesis into biomaterials (C. Johnson et al., Circulation Research 94 (2004), No. 2, 262-268).

In addition to, or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (for example, human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, for example, thrombin, fibrinogen, and the like. These substances may be applied to the ECM material as a premanufactured step, immediately prior to the procedure (for example, by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al., which is incorporated by reference herein. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example, less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

A preferred purification process involves disinfecting the submucosal tissue source, followed by removal of a purified matrix including the submucosa. It is thought that delaminating the disinfected submucosal tissue from the tunica muscularis and the tunica mucosa minimizes exposure of the submucosa to bacteria and other contaminants and better preserves the aseptic state and inherent biochemical form of the submucosa, thereby potentiating its beneficial effects. Alternatively, the ECM- or submucosa may be purified a process in which the sterilization step is carried out after delamination as described in U.S. Pat. Nos. 5,993,844 and 6,572,650.

The stripping of the submucosal tissue source is preferably carried out by utilizing a disinfected or sterile casing machine, to produce submucosa, which is substantially sterile and which has been minimally processed. A suitable casing machine is the Model 3-U-400 Stridhs Universal Machine for Hog Casing, commercially available from the AB Stridhs Maskiner, Gotoborg, Sweden. As a result of this process, the measured bioburden levels may be minimal or substantially zero. Other means for delaminating the submucosa source can be employed, including, for example, delaminating by hand.

Following delamination, submucosa may be sterilized using any conventional sterilization technique including propylene oxide or ethylene oxide treatment and gas plasma sterilization. Sterilization techniques which do not adversely affect the mechanical strength, structure, and biotropic properties of the purified submucosa are preferred. Preferred sterilization techniques also include exposing the graft to ethylene oxide treatment or gas plasma sterilization. Typically, the purified submucosa is subjected to two or more sterilization processes. After the purified submucosa is sterilized, for example, by chemical treatment, the matrix structure may be wrapped in a plastic or foil wrap and sterilized again using electron beam or gamma irradiation sterilization techniques.

Bioremodelable sheet materials, including ECMs according to the present invention, may be isolated and used in the form of intact natural sheets, tissue layers, or strips, which may be optimally configured from a native, wet, fluidized, or dry formulation or states, into sheets, knitted meshes, or porous scaffolds, using one or more of the following, including stretching, chemical crosslinking, lamination under dehydrating conditions, compression under dehydrating conditions, in accordance with teachings set forth in U.S. Pat. Nos. 6,206,931 and 6,358,284; U.S. Patent Application Publication Nos. 2006/0201996, 2006/0052816, 2005/0249772, and 2004/0166169, the disclosures of which are expressly incorporated by reference herein.

In addition, bioremodelable sheet materials according to the present invention may be treated by controlled autolysis to render the materials substantially acellular and less susceptible to post-implantation mineralization as described in U.S. Pat. Nos. 5,595,571, 5,720,777, 5,843,180, 5,843,181, and U.S. Patent Application Publication Nos. 2005/020612, the disclosures of which are expressly incorporated by reference herein.

Other Biocompatible Sheet Materials

Bioremodelable sheet materials provide a preferred source of biocompatible sheet materials connected to the occluding wires 18 in the occluding body 14. However, other biocompatible sheet materials may be used in addition to, or in place of, bioremodelable sheet materials, including composites thereof. Biocompatible sheet materials include a variety of natural or synthetic polymeric materials known to those of skill in the art which can be formed into flexible sheet materials covering the occluding body 14. Exemplary biocompatible sheet materials include polymeric materials, including textile materials; fibrous materials, including thrombogenic fibrous materials; and other biocompatible cover materials suitable for occlusion, which are known to those of skill in the art.

The biocompatible sheet materials may include porous or non-porous materials. When using non-bioremodelable synthetic sheet materials, the sheet materials are preferably made from porous materials, which can facilitate transfer of clotting factors and other bioactive agents associated with bioremodeling. A porous polymeric sheet may have a void-to-volume ratio from about 0.40 to about 0.90. Preferably the void-to-volume ratio is from about 0.65 to about 0.80. The resulting void-to-volume ratio can be substantially equal to the ratio of salt volume to the volume of the polymer plus the salt. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter may be measured based on images from a scanning electron microscope (SEM).

Biocompatible sheet materials may be formed from fibers, or any suitable material (natural, synthetic, or combination thereof) that is pliable, strong, resilient, elastic, and flexible. The material should be biocompatible or capable of being rendered biocompatible by coating, chemical treatment, or the like. Thus, in general, the material may comprise a synthetic biocompatible material that may include, for example, bioresorbable materials such as polylactic acid (PLA), polyglycolic acid (PGA), polycaprolactone (PCL), polydioxanone (PDO), trimethylene carbonate (TMC), polyvinyl alcohol (PVA), and copolymers or blends thereof; polyurethanes, including THORALON® (THORATEC, Pleasanton, Calif.), as described in U.S. Pat. Nos. 4,675,361, 6,939,377, and U.S. Patent Application Publication No. 2006/0052816, the disclosures of which are incorporated by reference herein; cellulose acetate, cellulose nitrate, silicone, polyethylene terephthalate, polyamide, polyester, polyorthoester, polyanhydride, polyether sulfone, polycarbonate, polypropylene, high molecular weight polyethylene, polytetrafluoroethylene, or mixtures or copolymers thereof, a polyanhydride, polycaprolactone, polyhydroxy-butyrate valerate, polyhydroxyalkanoate, or another polymer able to be made biocompatible.

Suitable biocompatible polyurethanes, including biocompatible polyurethanes sold under the trade name THORALON® (THORATEC, Pleasanton, Calif.), are described in U.S. Pat. Nos. 4,675,361 and 6,939,377, both of which are incorporated herein by reference. Briefly, these publications describe a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane containing polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON® has been used in certain vascular applications and is characterized by thromboresistance, high tensile strength, low water absorption, low critical surface tension, and good flex life. THORALON® is believed to be biostable and to be useful in vivo in long term blood contacting applications requiring biostability and leak resistance. Because of its flexibility, THORALON® has been particularly useful in larger vessels, such as the abdominal aorta, where elasticity and compliance is beneficial.

THORALON® can be manipulated to provide either porous or non-porous THORALON®. Formation of porous THORALON® is described, for example, in U.S. Pat. No. 6,752,826 and 2003/0149471 A1, both of which are incorporated herein by reference. Porous THORALON® can be formed by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. Examples of solvents include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than about 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting void-to-volume ratio can be substantially equal to the ratio of salt volume to the volume of the polymer plus the salt. The resulting pore diameter can also be substantially equal to the diameter of the salt grains.

A variety of other biocompatible polyurethanes may be employed in the above-described materials. These include polyurethane ureas that preferably include a soft segment and a hard segment formed from a diisocyanate and diamine. For example, polyurethane ureas with soft segments such as polytetramethylene oxide (PTMO), polyethylene oxide, polypropylene oxide, polycarbonate, polyolefin, polysiloxane (i.e. polydimethylsiloxane), and other polyether soft segments made from higher homologous series of diols may be used. Segments can be combined as copolymers or as blends. Mixtures of the soft segments may also be used. The soft segments also may have either alcohol end groups or amine end groups. The molecular weight of the soft segments may vary from about 500 to about 5,000 g/mole.

The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethyhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

The hard segment may be formed from one or more polyols. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible polyurethanes modified with cationic, anionic and aliphatic side chains may also be used. See, for example, U.S. Pat. No. 5,017,664.

Other biocompatible polyurethanes include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible polyurethanes include polyurethanes having a siloxane segment, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

Biocompatible polyurethanes may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

The polymeric materials may include a textile material. The textile includes fibers and may take many forms, including woven (including knitted) and non-woven. Preferably, the fibers of the textile comprise a synthetic polymer. Polymeric materials that can be formed into fibers suitable for making textiles include polyethylene, polypropylene, polyaramids, polyacrylonitrile, nylons and cellulose, in addition to polyesters, fluorinated polymers, and polyurethanes as listed above. Additionally preferred textiles include those formed from polyethylene terephthalate, polytetrafluoroethylene (PTFE), expanded polytetrafluoroethylene (ePTFE), PTFE, and polyesters. These materials are inexpensive, easy to handle, have good physical characteristics and are suitable for clinical application. Examples of biocompatible polyesters include DACRON (DUPONT, Wilmington, Del.) and TWILL-WEAVE MICREL (VASCUTEK, Renfrewshire, Scotland).

Films or sheets of ePTFE are typically porous without the need for further processing. The structure of ePTFE can be characterized as containing nodes connected by fibrils. Porous ePTFE can be formed, for example, by blending PTFE with an organic lubricant and compressing it under relatively low pressure. Using a ram type extruder, the compressed polymer is then extruded through a die, and the lubricant is removed from the extruded polymer by drying or other extraction method. The dried material is then rapidly stretched and/or expanded at elevated temperatures. This process can provide for ePTFE having a microstructure characterized by elongated nodes interconnected by fibrils. Typically, the nodes are oriented with their elongated axis perpendicular to the direction of stretch. After stretching, the porous polymer is sintered by heating it to a temperature above its crystalline melting point while maintaining the material in its stretched condition. This can be considered as an amorphous locking process for permanently setting the microstructure in its expanded or stretched configuration. The structure and porosity of ePTFE is disclosed, for example, in U.S. Pat. Nos. 6,547,815 B2; 5,980,799; and 3,953,566; all of which are incorporated herein by reference. Structures of porous hollow fibers can be formed from PTFE, and these porous hollow fibers can be assembled to provide a cohesive porous sheet or polymeric coating. Porous hollow fibers containing PTFE are disclosed, for example, in U.S. Pat. No. 5,024,671, which is incorporated herein by reference.

Thrombogenic fibrous materials include synthetic or natural fibrous material having thrombogenic properties. Exemplary thrombogenic fibrous materials include, but are not limited to, DACRON (DUPONT, Wilmington, Del.), cotton, silk, wool, polyester thread and the like.

Textile materials may be woven (including knitted) textiles or nonwoven textiles. Nonwoven textiles are fibrous webs that are held together through bonding of the individual fibers or filaments. The bonding can be accomplished through thermal or chemical treatments or through mechanically entangling the fibers or filaments. Because nonwovens are not subjected to weaving or knitting, the fibers can be used in a crude form without being converted into a yarn structure. Woven textiles are fibrous webs that have been formed by knitting or weaving. The woven textile structure may be any kind of weave including, for example, a plain weave, a herringbone weave, a satin weave, or a basket weave.

Woven fabrics may have any desirable shape, size, form and configuration. For example, the fibers of a woven fabric may be filled or unfilled. Examples of how the basic unfilled fibers may be manufactured and purchased are indicated in U.S. Pat. No. 3,772,137, by Tolliver, disclosure of which is incorporated by reference. Fibers similar to those described are currently being manufactured by the DuPont Company from polyethylene terephthalate (often known as "DACRON" when manufactured by DuPont), and by other companies from various substances.

Preferably the textile is made of one or more polymers that do not require treatment or modification to be biocompatible. However, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile material, provided the final textile is biocompatible.

Non-Native Bioactive Agents

Non-native bioactive agents, such as those synthetically produced by recombinant technology or other methods, may be incorporated into any of the above-described biocompatible materials. The bioactive agent may be biochemical, organic, inorganic or synthetic in nature. Preferably the bioactive agent will be thrombogenic, fibrogenic, angiogenic, antithrombolytic, antifibrinolytic, fibrin stabilizing, wound healing, fibroblast stimulatory, vascularization promoting, cell and/or tissue attachment promoting, extracellular matrix promoting and/or the like. The bioactive agent may be a protein, peptide, growth factor, peptidomimetic, organic molecule, drug, antibiotic agent, biocidal agent, synthetic molecule, synthetic polymer, or the like. Preferably, the bioactive agent will accelerate or support thrombosis, fibrosis, deposition of connective tissue (e.g., collagen etc) in or around the closure device and/or stronger anchoring of the closure device to surrounding tissues. The non-native bioactive agents may be naturally-derived or recombinantly produced proteins, such as growth factors, which are normally found in ECM tissues. These proteins may be obtained from or engineered from any animal species. The non-native bioactive agents may also be drug substances, including antibiotics and the like.

Bioactive agents that may be incorporated into or onto ECM materials used in the invention include, for example, antibiotics or thrombus-promoting substances such as blood clotting factors, for example, thrombin, fibrinogen, and the like. These substances may be applied to the biocompatible material as a premanufactured step, immediately prior to the procedure (for example, by soaking the material in a solution containing a suitable antibiotic such as cefazolin), or during or after engraftment of the material in the patient. Alternatively, the bioactive agent(s) may be incorporated into the pores of porous polymeric materials and/or they may be chemically bonded to the biocompatible material or polymer backbone using e.g., chemical cross-linking agents or other means conventionally available to those of skill in the art. By way of example, bioactive agent(s) may be embedded into the pores of the polymeric material in a range between about 0.005% w/w and 50% w/w, between about 0.05% and 10% w/w, between about 0.1% w/w and 2% w/w, between about 0.25% w/w and 1% w/w and combinations of ranges therefrom.

Exemplary bioactive agents include, but are not limited to, clotting factors, including, but not limited to plasmin, thrombin, prothrombin, fibrinogen, Factor V, Factor Va, Factor VII, Factor VIIa, Factor VIII, Factor VIIIa, Factor IX, Factor IXa, Factor X, Factor Xa, Factor XI, Factor XIa, Factor XII, XIIa, Factor XIII, von Willebrand Factor (vWF), other coagulation cascade factors and derivatives (e.g., natural, synthetic, recombinant etc.) therefrom; antifibrinolytic agents, including, but not limited to, aminocaproic acid, aprotinin, tranexamic acid, desopressin, etamsylate; integrins; peptides containing RGD (arginine-glycine-aspartic acid) residues; cell attachment factors, including, but not limited to collagen (Types I-XIV), elastin, fibronectin, laminin, vitronectin; homocysteine; growth factors, including, but not limited to Connective Tissue Growth Factor (CTGF), Vascular Endothelial Growth Factor (VEGF), Platelet Derived Growth Factor (PDGF), Fibroblast Growth Factor (FGF), Keratinocyte Growth Factor (KGF), Tumor Necrosis Factor (TNF), Epidermal Growth Factor (EGF), Transforming Growth Factor-alpha (TGF-$\alpha$), Transforming Growth Factor-beta (TGF-$\beta$); cytokines, interleukins (e.g., IL-1, -2, -6, -8 etc.), chemokines having the above described chemical or biological properties. The biocompatible material may hold a single bioactive agent or a plurality of bioactive agents, as in the form of e.g., a cocktail.

Closure Device Assembly

In a further aspect, a closure assembly 40 for delivering a closure device according to the present invention is provided. The closure device assembly 40 includes a delivery catheter 80, an anchor engaging member 82, and a closure device 10. Any of the above-described closure devices 10 may be used. Generally, the closure device 10 includes an occluding body 14 comprised of a plurality of flexible outwardly radiating occluding wires 18 connected to biocompatible or bioremodelable sheet material 22. The occluding wires 18 are joined together at proximal wire ends. Preferably, a clamp 26 is used to secure the proximal wire ends. The occluding body 14 is connected to one or more anchors 30 by one or more linking members 54. An anchor 30 includes a coil 34 and one or more grasping member(s) 50, whereby one or more of the grasping member(s) 50 is connected to the anchor engaging member.

In a preferred embodiment, the anchor engaging member 82 is positioned in a locking catheter 86 configured to prevent inadvertent release of the closure device 10 when held in a compressed state inside the delivery catheter 80.

Figure 5A:
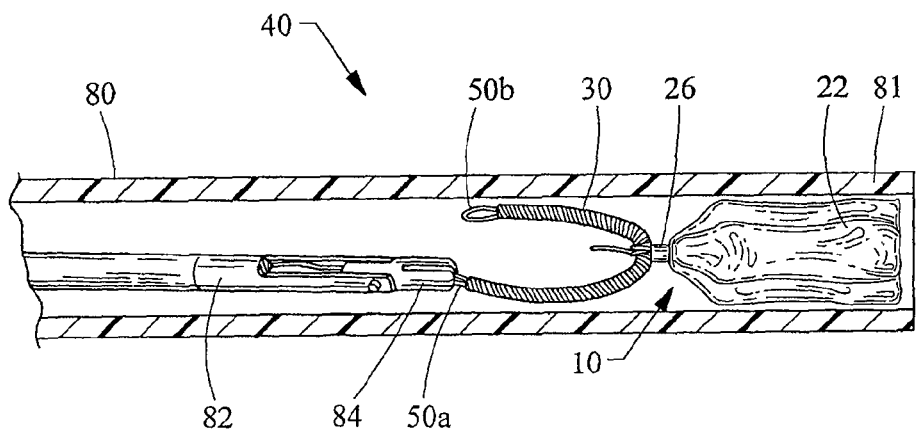
FIG. 5A shows a closure device assembly according to an embodiment of the present invention.
Figure 5B:
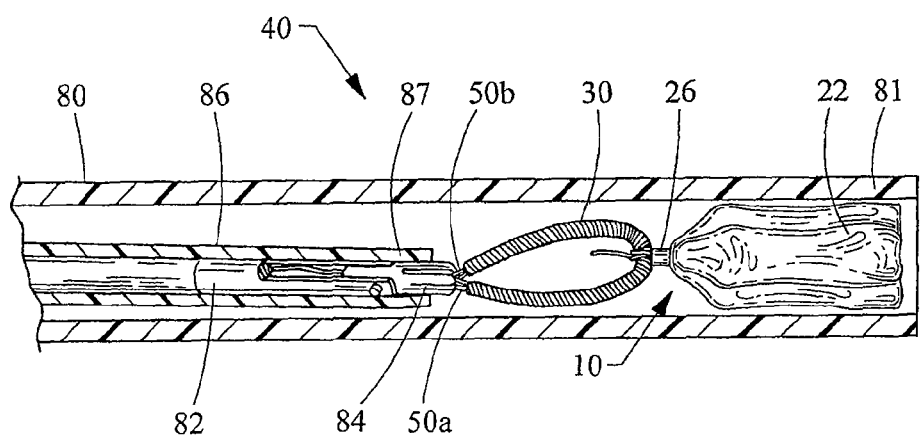
FIG. 5B shows a closure device assembly according to another embodiment of the present invention.

FIGS. 5A and 5B depict exemplary closure device assemblies 40 facilitating rapid deployment of the closure device 10. In FIG. 5A, the closure device assembly 40 includes a delivery catheter 80 containing a preloaded, collapsibly disposed closure device 10 disposed near the distal tip of the delivery catheter 80. Any of the above-described closure devices 10 may be used in the assemblies described herein.

The assembly 40 further includes an anchor engaging member or biopsy forceps 82 securely linked to one or more grasping member(s) 50a, 50b in the anchor 30 of the closure device 10. This linkage facilitates positioning and uncoupling of the closure device 10 from the delivery catheter 80 in connection with closure device 10 deployment. FIG. 5A depicts an anchor engaging member as a biopsy forceps 82 linked to a single loop structure 50a.

The anchor engaging member 82 includes an anchor engagement portion 84 releasably attached to one or more grasping member(s) 50a, 50b. In a preferred embodiment, the anchor engaging member 82 comprises biopsy forceps containing anchor engagement portions in the form of cups or jaws 84. The anchor engaging member 82 includes an anchor engagement portion 84 having a structure complementary to the grasping member 50a, which is configured for releasable attachment thereto. The anchor engagement portion 84 may include a ball, hook, loop, pair of cups or jaws, or other suitable complementary structure capable of releasable attachment to one or more grasping member(s) 50. In a preferred embodiment, the anchor engaging member 82 comprises biopsy forceps.

In FIG. 5A, the grasping member is depicted as a loop structure 50a connected to a biopsy forceps 82 by way of an anchor engagement portion 84 depicted as a pair of cups. The anchor engagement portion 84 may include a ball, hook, loop, a pair of cups or jaws, or any other configuration suitable for releasable attachment to one or more grasping member(s) 50.

The delivery catheter 80 may be configured for "long wire" or "over-the-wire" (OTW) delivery or for "short wire" or rapid exchange (RE) delivery procedures known to those of skill in the art. Accordingly, the delivery catheter 80 may be structurally modified with apertures and/or modified lumenal portions to allow exchange from, for example, a multi-purpose guide catheter to the delivery catheter 80 by RE without the need to replace the wire guide with an exchange-length guide wire before exchanging the catheters. Exemplary RE catheters that may be used to deliver the closure device 10 of the present invention are described in U.S. Pat. Nos. 5,690, 642; 5,814,061; 6,371,961; and U.S. Pat. Application Nos. 2005/0070794; 2005/0125050; and 2005/0070821, the disclosures of which are expressly incorporated by reference herein.

FIG. 5B further depicts an additional safety feature preventing premature disengagement of the closure device from the anchor(s) 30 prior to or during release of some or all of the device 10 from the delivery catheter 82. In this embodiment, the biopsy forceps 82 is passed through a smaller, coaxially positioned locking catheter 86. The biopsy cups 84 of the biopsy forceps 82 are connected to two terminally disposed loop structures 50a, 50b in the anchor 30. The locking catheter 86 and the biopsy forceps 82 are configured so that the biopsy cups (or jaws) 84 are prevented from inadvertently releasing the closure device 10 while positioned inside the delivery catheter 80. In particular, the distal end of the locking catheter sheath 87 overhangs a portion of the biopsy cups 84, thereby preventing premature disengagement of the anchor (s) 30 from the biopsy forceps 82 prior to or during release of some or all of the device 10 from the delivery catheter 80.

In a preferred embodiment, the anchor engaging member comprises biopsy forceps 82 containing anchor engagement portions in the form of jaws or cups 84. Suitable biopsy forceps for use in the present invention include Cup Biopsy Forceps (Cook Urological, Inc., Spencer, Ind.) and Biopsy Cup Forceps (ACMI Corp., Southborough, Mass.).

The closure device 10 is made from sufficiently flexible materials to enable the device 10 to be collapsibly disposed within a relatively small delivery catheter 80 (including 5 to 8 French). The closure device 10 may be preloaded at the tip of the delivery catheter 80 in an unexpanded, first configuration. When the closure device 10 is expelled from the delivery catheter 80, it may expand to a second, expanded configuration, particularly when the closure device 10 is made from shape memory materials. Non shape memory materials, such as stainless steel and the like, may be used for closure devices 10 requiring a lower degree of compression or expansion upon release.

In a preferred embodiment, the closure device assembly 40 includes a delivery catheter 80 with a curved sheath, and a collapsibly disposed closure device 10 preloaded near the tip of the delivery catheter sheath 81, whereby the closure device 10 is connected to a biopsy forceps 82 held within a locking catheter 86. In a particularly preferred embodiment, the closure device assembly 40 includes a curved 5, 6, 7, or 8 French delivery catheter 80; a 4 or 5 French locking catheter 86 holding the biopsy forceps 82; and a collapsibly disposed closure device 10. Flexor® Introducer Sets (Cook Medical Inc., Bloomington, Ind.) provide a preferred source of delivery catheters for use in the present invention.

To enhance the shelf life of the closure device containing bioremodelable materials, the device 10 may be lyophilized in an elongated form inside a cartridge sheath having a similar inner diameter sheath size as the delivery catheter 80 (for example, 5-8 French size). In view of their low device profile, it is believed that closure devices 10 of the present invention can be delivered and securely deployed from a single, tip preloaded delivery catheter 80 for immediate and complete passageway closure in as little as 15 minutes.

Method For Closing A Bodily Opening

In a further aspect, the present invention provides a method for closing or occluding a bodily opening in a patient using a closure device 10 or closure device assembly 40 as described above. In a preferred embodiment, a method for closing or occluding a septal opening, such as a PFO using the above described closure device assembly is provided.

By way of example, FIGS. 6A-6D depict a method for closing a PFO with a closure device assembly 40 according to the present invention. In this example, multiple delivery components are included in the closure device assembly 40 to allow completion of the deployment process in as little as 10-15 minutes.

The closure device assembly 40 includes a delivery catheter 80, a closure device 10 collapsibly disposed therein, and an anchor engaging member 82 facilitating closure device 10 delivery. Any of the above described closure devices 10 may be used. In general, the closure device includes an occluding body 14 connected to one or more anchor(s) 30. The occluding body 14 is comprised of outwardly radiating occluding wires 18 configured to be inwardly biased against tissues portions surrounding a bodily passageway. The occluding wires 18 are held together at one end by a clamp 26. The anchor(s) 30 are connected to the anchor engaging member 82 (herein depicted as biopsy forceps). The anchor(s) 30 includes two terminally disposed grasping members 50 (herein depicted as wire loop structures) for releasable attachment to the anchor engagement portion 84 (herein depicted as cups or jaws) of the biopsy forceps 82.

To prevent inadvertent release of the closure device 10 from the anchor engaging member 82 when held in a compressed state inside the delivery catheter 80, the anchor engaging member 82 is preferably positioned in a locking catheter 86. Preferably, the closure device 10 of the present invention is collapsibly disposed near the tip of the delivery catheter sheath 81.

Figure 6A:
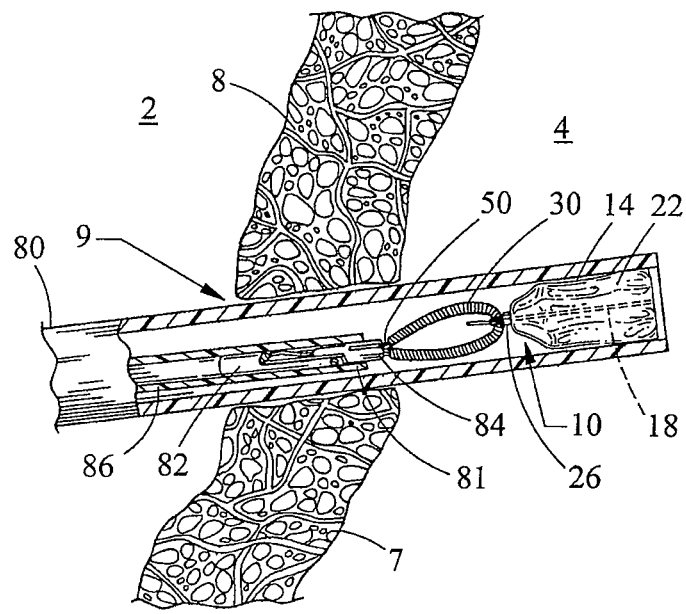
FIG. 6A shows a cross-sectional view of the distal end of the closure device assembly of FIG. 5B inserted and extending through a PFO.
Figure 6B:
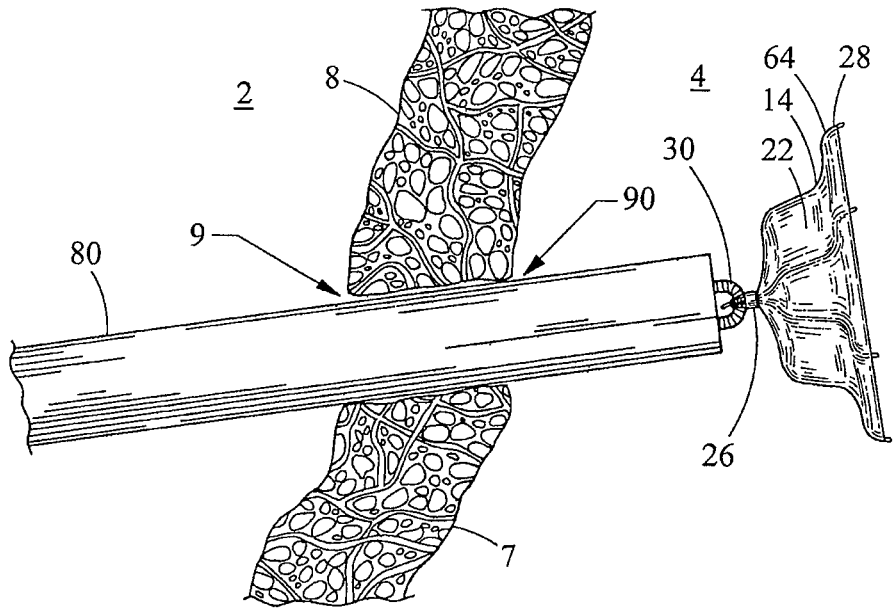
FIG. 6B shows a cross-sectional view of the distal end of the closure device assembly of FIG. 5B extending through a PFO and releasing an occluding body proximal to the distal PFO opening.

A stiff guide wire is passed through a diagnostic multipurpose catheter, which has been positioned in the left atrium across a bodily passageway, such as a PFO. The delivery catheter 80 of the closure device assembly 40 is introduced over the wire and positioned into the left atrium 4 of a patient, through the passageway of the PFO 9 (FIGS. 1, 6A). Before releasing the device 10 or any part thereof, its position may be assessed by contrast media injection though the delivery catheter 80. The closure device 10 is self-expanding and retains its original shape in the left atrium 4 upon its release from the delivery catheter 80 proximate to the distal opening 90 of the PFO 9 (FIG. 6B). Following release of the occluding body 14 from the distal end of the delivery catheter 80, the delivery catheter 80 is retracted through the opening of the PFO 9, thereby pulling the rib-like skeleton of occluding wires 18 against the septum primum 7 and the septum secundum 8 (FIG. 6C). The occluding wires 18 may additionally include curved wire ends 64 inwardly biased against portions of the septum primum 7 and the septum secundum 8 to facilitate more secure anchoring thereto. The delivery catheter 80 is retracted into the right atrium 2, positioning the flexible anchor(s) 30 at the distal end of the delivery catheter 80 near the proximal opening 92 of the PFO 9. Following confirmation of right atrium 2 positioning, the locking catheter 86 is advanced toward the distal end of the delivery catheter 80 and the locking catheter sheath 87 is pulled back, the biopsy cups 84 of the biopsy forceps 82 can be released from the loop structures 50 in the anchor 30, thereby releasing the anchor 30 into the right atrium 2 near the proximal opening 92 of the PFO 9 (FIG. 6D). Upon release from the delivery catheter 80, the anchor 30 linearly expands and springs back against the septum primum 7 and septum secundum 8, anchoring the occluding body 14 (and occluding device 10) through the PFO 9 (FIG. 6E). The delivery catheter 80, locking catheter 86, and biopsy forceps 82 are then retracted and removed.

As an alternative to the pre-assembled, over-the-wire delivery process described above, one can alternatively introduce and position a wire guide through, for example, a guiding catheter near the site of the passageway opening; load the collapsible closure device 10 into the guiding catheter or sheath; and push the closure device 10 to the desired site with a suitable biopsy forceps, pushing catheter or other suitable pushing device.

Preferably, the deployed closure device 10 includes submucosal tissue that is configured to stimulate angiogenesis. In addition, the closure device 10 is preferably implanted so that the closure 10 occludes all or at least a portion of the bodily passageway, whereby the submucosal tissue is stably absorbed and replaced by host tissues.

As an alternative to the above method, the closure device 10 may be deployed whereby the anchor 30 is released first, followed by the occluding body 14 analogously linked, in this case, to one or more grasping member(s) disposed therein for attachment to a biopsy forceps 82 or other suitable engagement member.

Visualization of the assembly 40 within the interior of the heart during deployment may be provided by various means. For example, fluoro-visible (i.e. radio-opaque) dyes may be injected into the cardiac chambers and venous anatomy so that the chambers of the heart and the related vasculature are visible using a fluoroscopic device. This procedure, sometimes referred to as a venogram, allows the surgeon to locate a precise site and achieve proper device placement when performing an implant procedure.

Additionally, an ultrasonic probe may be positioned in the patient's esophagus, on the surface of the patient's chest, or in the chest cavity adjacent or in contact with the exterior of the heart to ultrasonically image the interior of the heart. In particular an intravascular ultrasound (IVUS) catheter may be utilized in conjunction with the above assembly 40 to provide ultrasonic imaging. Alternatively, an endoscope with a translucent bulb or balloon over its distal end may be introduced into the heart through the closure device assembly and/or through a separate incision in the wall of the heart to allow video-based or direct visualization of the interior of the heart. An angioscope introduced into the heart endovascularly through a peripheral vessel may also be used for intracardiac visualization. Fluoroscopy or magnetic resonance imaging (MRI) may provide an additional means for visualization.

Sheaths, dilators, catheters, guide catheters, pushing catheters, wire guides, and needles used in the present invention can all be conventional marketed products or modifications thereof. For example, sheaths can be formed from PTFE (e.g. Teflon) or polyamide (e.g. Nylon) material, or a combination of materials such as an assembly including an inner layer of PTFE, a flat wire coil over the PTFE for kink resistance, and a polyamide (Nylon) outer layer to provide integrity to the overall structure and a smooth surface (as in the Flexor® Introducer Sets, Cook Medical Inc., Bloomington, Ind.). Dilators can be made from conventional dilator/catheter type materials such as polyethylene, polyamide, polyurethane or vinyl, or any combination of these materials. Fittings provided for sheath/dilator assemblies can be conventional elements such as luer locks; the dilator and the locking catheter can have fittings allowing them to be locked to the sheath during insertion and manipulation. Catheters can be made from conventional materials such as polyethylene, polyamide, PTFE, polyurethane, and other materials. Assembly components, including guide wires and biopsy forceps may be individually contained in interlumenal sheaths within the delivery catheter or they may be disposed through secondary lumenal portions formed in the delivery catheter, as in double lumen catheters and the like.

The delivery catheter includes a sheath having a lumen diameter sized to allow for the introduction of the closure device to occlude the bodily passageway of interest. Illustratively, the inner diameter (I.D.) of the delivery sheath may range from about 6 to 10 French or more, depending on the size of the closure device and the bodily passageway for closure. In preferred embodiments the delivery catheter includes a 5-8 French inner sheath diameter (i.e., 0.074 inches to 0.113 inches).

Radiopaque marker materials may be added to one or more components of the closure device 10 and/or assembly 40 so as to render them radiopaque or MRI compatible. In particular, radiopaque materials, fillers, metallic marker bands or powders may be included into one or more of the occluding body 14, including the occluding wires 18, biocompatible sheet materials 22, and clamp 26; anchor 30; coil 34; anchor wire(s) 46, delivery catheter 80, and locking catheter 86 (including any component parts therein) to facilitate radiographic visualization of the device during the implantation process. In preferred embodiments, the occluding wire 18 ends, clamp 26, coil 34, anchor wire 46, or combinations thereof, include or are made from platinum.

Exemplary radiopaque marker materials include but are not limited to, platinum, gold, tungsten, tantalum, tantalum powder, bismuth, bismuth oxychloride, barium, barium sulphate, iodine and the like. Metallic bands of stainless steel, tantalum, platinum, gold, or other suitable materials, can include a dimple pattern, which can further facilitate ultrasound and/or X-ray identification.

Radiopaque markers may be introduced in any form suitable for the rendering the closure device radiopaque or MRI compatible. In addition, the radiopaque materials can be incorporated in the closure device or assembly components by a variety of common methods, such as adhesive bonding, lamination between two material layers, vapor deposition, and the materials and methods described in U.S. 2003/0206860, the disclosure of which is incorporated herein by reference.

A closure device 10 or assembly 40 according to the present invention is particularly suited for closing septal heart defects, including PFOs and other atrial septal or ventricular septal defects. However, the closure device 10 can be similarly applied to closing or occluding a variety of other heart openings, tissue openings, vessels, vessel punctures, ducts, and other tissue openings where closure is desired.

Closure Device Repositioning or Removal

In some instances it may be necessary to remove the closure device. This may occur where the device is not appropriately sized for a particular bodily passageway and/or fails to completely seal the passageway. In cases where it is necessary or advisable to reposition or remove the closure device 10, a suitable foreign body retrieval device, such as a snare, may be used to reposition or remove devices, especially those containing sufficiently flexible materials or structural configurations. The snare may be delivered through the introducer sheath using a snare catheter. Preferred snares are commercially available under the trade name Needle's Eye® Snare (Cook Medical, Bloomington, Ind.) and Amplatz Goose Neck® Snare (ev3 Inc., Plymouth, Minn.).

It is intended that the foregoing detailed description be regarded as illustrative rather than limiting, and that it be understood that it is the following claims, including all equivalents, that are intended to define the spirit and scope of this invention.

The invention claimed is:

1. A closure device for occluding a bodily passageway having a proximal end and a distal end, comprising:
   an occluding body comprising a plurality of flexible outwardly radiating occluding wires having a collapsed configuration for delivery or retrieval and an expanded configuration for occluding the bodily passageway, the occluding wires connected to one or more biocompatible sheet materials, wherein the occluding wires are joined together at proximal wire ends and include proximal wire portions provided adjacent to the proximal wire ends, the proximal wire portions configured to be placed within the bodily passageway and to be biased against tissue portions within the bodily passageway, wherein in the expanded configuration, each occluding wire has an inward first bend portion in the proximal portion and an outward second bend portion extending from the first bend portion to a distal free end;
   a clamp located along a central axis of the closure device, the clamp securing the proximal wire ends; and
   an elongated anchor forming a single flexible, substantially linear structure comprising at least one tube, coil, or bar, and having two anchor ends;
   wherein the occluding body is connected to a center region of the substantially linear structure by at least one linking member; and
   wherein the anchor extends in a direction transverse to and across the central axis of the occluding device and is configured to extend radially beyond the first bend portion and beyond a transverse cross-section of the bodily passageway with both anchor ends, the anchor anchoring the occluding body into the bodily passageway.

2. The device of claim 1, wherein the anchor comprises a grasping member integrally formed therein.

3. The device of claim 1, wherein the anchor comprises a grasping member connected thereto.

4. The device of claim 1, wherein the anchor comprises a grasping member comprising a terminally disposed structure selected from the group consisting of a loop, ball, hook, or knob.

5. The device of claim 1, wherein the anchor comprises a hollow structure having an anchor wire longitudinally extending therethrough.

6. The device of claim 1, wherein the anchor comprises a coil defined by a first end and a second end, wherein an anchor wire extends longitudinally through the coil, the wire comprising at least one terminally disposed grasping member.

7. The device of claim 1, wherein the at least one linking member comprises a suture or wire.

8. The device of claim 1, wherein the occluding wires comprise Nitinol.

9. The device of claim 1, wherein the anchor comprises platinum.

10. The device of claim 1, wherein the biocompatible material comprises bioremodelable sheet material.

11. The device of claim 1, wherein the biocompatible material is selected from the group consisting of DACRON, PTFE, ePTFE, polyurethane, cotton, silk, wool, polyester, and combinations thereof.

12. The device of claim 1, wherein the occluding wires include distal wire portions opposing the proximal wire portions, the proximal wire portions configured for placement inside the bodily passageway and the distal wire portions configured for placement outside the bodily passageway.

13. The device of claim 1, wherein the proximal wire portions comprise an arcuate conformation adjacent to the proximal end of the bodily passageway.

14. The device of claim 1, wherein the occluding wires further include distal wire portions, wherein the distal wire portions comprise an arcuate conformation configured for placement outside the distal end of the bodily passageway and to be inwardly biased against tissue portions surrounding the distal end of the bodily passageway.

15. A closure device assembly comprising:
   a delivery catheter, an anchor engaging member, and a closure device for occluding a bodily passageway having a proximal end and a distal end, the closure device comprising:
      an occluding body comprising a plurality of flexible outwardly radiating occluding wires having a collapsed configuration for delivery or retrieval and an expanded configuration for occluding the bodily passageway, the occluding wires connected to one or more biocompatible sheet materials, wherein the wires are joined together at proximal wire ends and include proximal wire portions provided adjacent to the proximal wire ends, the proximal wire portions configured to be placed inside the bodily passageway and to be biased against tissue portions within the bodily passageway, wherein in the expanded configuration, each occluding wire has an inward first bend portion in the proximal portion and an outward second bend portion extending from the first bend portion to a distal free end;
      a clamp located along a central axis of the closure device, the clamp securing the proximal wire ends; and
      an elongated anchor forming a single flexible and linear structure having two anchor ends and disposed adjacent to the proximal wire ends, wherein the occluding body is connected to a center region of the substantially linear structure by at least one linking member, the anchor extends in a direction transverse to and across the central axis of the occluding device and configured to extend radially beyond the first bend portion and beyond a transverse cross-section of the bodily passageway with both anchor ends, the anchor anchoring the occluding body into the bodily passageway, wherein the anchor in the closure device is connected to the anchor engaging member.

16. The closure device assembly of claim 15, wherein the anchor engaging member comprises biopsy forceps.

17. The closure device assembly of claim 15, wherein the delivery catheter further houses a locking catheter housing the anchor engaging member.

18. The closure device assembly of claim 17, wherein the locking catheter is secured to the anchor engaging member so that the closure device is prevented from being released inside of the delivery catheter.

19. The device of claim 1, wherein the bodily passageway is a patent foramen ovale.

20. A closure device for occluding a bodily passageway having a proximal end and a distal end, comprising:

an occluding body comprising a plurality of flexible outwardly radiating occluding wires having a collapsed configuration for delivery or retrieval and an expanded configuration for occluding the bodily passageway, the wires having proximal wire ends secured together at a clamp located along a central axis of the closure device, wherein in the expanded configuration, each occluding wire has an inward first bend portion in the proximal portion and an outward second bend portion extending from the first bend portion to a distal free end;

at least one biocompatible sheet connected to the occluding body; and an elongated anchor forming a single flexible, substantially linear structure comprising at least one tube, coil, or bar, and having two anchor ends;

wherein the occluding body is connected to a center region of the substantially linear structure by at least one linking member; and wherein the anchor extends in a direction transverse to and across the central axis of the occluding device and is configured to extend radially beyond the first bend portion and beyond a transverse cross-section of the bodily passageway with both anchor ends, the anchor anchoring the occluding body into the bodily passageway.

* * * * *

UNITED STATES PATENT AND TRADEMARK OFFICE
CERTIFICATE OF CORRECTION

PATENT NO. : 8,734,483 B2
APPLICATION NO. : 11/845423
DATED : May 27, 2014
INVENTOR(S) : Tekulve et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1323 days.

Signed and Sealed this
Twenty-eighth Day of July, 2015

Michelle K. Lee
*Director of the United States Patent and Trademark Office*